United States Patent [19]

Cherry et al.

[11] Patent Number: 4,798,893

[45] Date of Patent: Jan. 17, 1989

[54] PROCESS FOR PRODUCING 1-(5-SUBSTITUTED-2-ETHYNYLPHENYL)-2-PROPANONES

[75] Inventors: David A. Cherry, Ambler; Cynthia A. Maryanoff, Solebury Township; John E. Mills, Hatfield; Roy A. Olofson, State College; James D. Rodgers, North Wales, all of Pa.

[73] Assignee: McNeilab, Inc., Springhouse, Pa.

[21] Appl. No.: 99,427

[22] Filed: Sep. 21, 1987

[51] Int. Cl.[4] .............. C07D 251/16; C07D 251/20; C07C 69/78; C07C 49/217
[52] U.S. Cl. ..................... 544/215; 544/180; 544/182; 544/194; 544/197; 544/198; 544/208; 544/209; 544/211; 544/212; 544/224; 544/240; 544/239; 544/238; 544/296; 544/299; 544/300; 544/301; 544/302; 544/309; 544/310; 544/311; 544/312; 544/314; 544/315; 544/316; 544/317; 544/318; 544/319; 544/321; 544/322; 544/323; 544/324; 544/325; 544/326; 544/328; 544/329; 544/330; 544/331; 544/332; 544/333; 544/335; 544/336; 544/357; 544/405; 544/406; 546/261; 546/262; 546/263; 546/264; 546/265; 546/267; 546/275; 546/276; 546/277; 546/278; 546/279; 546/280; 546/281; 546/283; 546/284; 546/286; 546/287; 546/288; 546/289; 546/291; 546/292; 546/296; 546/297; 546/298; 546/300; 546/301; 546/304; 546/307; 546/308; 546/309; 546/310; 546/312; 546/329; 546/330; 546/334; 546/335; 546/337; 546/342; 548/127; 548/128; 548/182; 548/183; 548/184; 548/185; 548/187; 548/188; 548/190; 548/191; 548/194; 548/225; 548/226; 548/227; 548/228; 548/229; 548/230; 548/232; 548/233; 548/235; 548/236; 548/243; 548/244; 548/245; 548/246; 548/247; 548/248; 548/255; 548/262; 548/263; 548/264; 548/265; 548/266; 548/267; 548/268; 548/341; 548/342; 548/343; 548/336; 548/337; 548/374; 548/375; 548/376; 548/377; 548/378; 548/518; 548/519; 548/520; 548/522; 548/527; 548/531; 548/532; 548/540; 548/541; 548/543; 548/544; 548/545; 548/546; 548/547; 548/551; 548/556; 548/557; 548/558; 548/560; 548/562; 560/108; 560/138; 568/325

[58] Field of Search ............ 549/59, 61, 62, 68, 549/69, 75, 78, 475, 478, 479, 480, 483, 484, 491, 496, 498, 501; 548/518, 527, 519, 520, 522, 531, 532, 540, 541, 543, 544, 545, 546, 547, 551, 556, 557, 558, 560, 562, 374, 375, 376, 377, 378, 336, 337, 341, 342, 343, 255, 262, 263, 264, 265, 266, 267, 268, 225, 226, 227, 228, 229, 230, 232, 233, 235, 236, 243, 244, 245, 246, 247, 248, 182, 183, 184, 185, 187, 188, 190, 191, 192; 548/194, 127, 128, 129, 130; 546/261, 262, 263, 264, 265, 267, 275, 276, 277, 278, 279, 280, 281, 283, 284, 286, 287, 288, 289, 291, 292, 296, 297, 298, 300, 301, 304, 307, 308, 309, 310, 312, 329, 330, 334, 335, 337, 342; 544/357, 405, 406, 408, 336, 296, 299, 300, 301, 302, 309, 310, 311, 312, 314, 315, 316, 317, 318, 319, 321, 322, 323, 324, 325, 326, 328, 329, 330, 331, 332, 333, 335, 238, 239, 240, 224, 180, 182, 194, 197, 198, 208, 209, 211, 212; 560/108, 138; 568/325

[56] References Cited

U.S. PATENT DOCUMENTS 4,614,546  9/1986  Schroer et al. ............ 106/213
4,661,635  4/1987  Carson ..................... 564/374
4,701,540 10/1987  Lukac et al. ............... 549/341

Primary Examiner—Mary C. Lee
Assistant Examiner—J. Richter
Attorney, Agent, or Firm—David J. Levy

[57] ABSTRACT

A method for the synthesis of the 2-propanone (I) is described starting from alkoxide (II) through the lactone (IV).

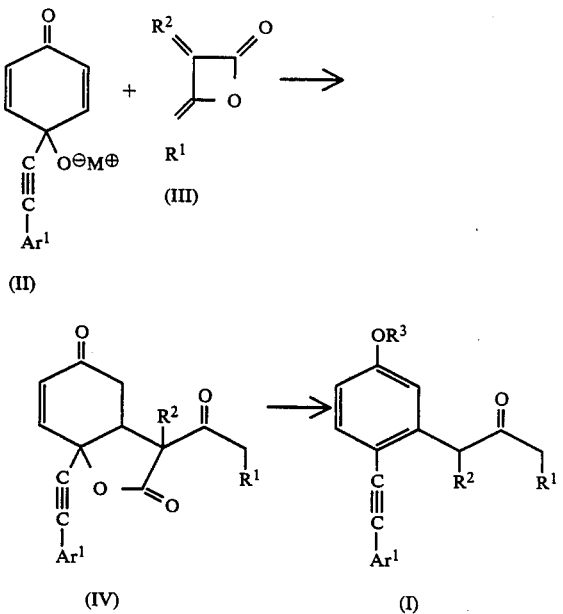

Excellent control of the location of the substitution on the phenyl ring is achieved and the reaction proceeds in high yield.

13 Claims, No Drawings

PROCESS FOR PRODUCING 1-(5-SUBSTITUTED-2-ETHYNYLPHENYL)-2-PROPANONES

BACKGROUND OF THE INVENTION

U.S. Pat. No. 4,661,635 to Carson describes acetylenic calcium blockers useful as antihypertensives and/or antianginals. Several synthetic routes are set forth and a prime intermediate is a 1-(5-substituted-2-ethynylphenyl)-2-propanone such as 1-[5-methoxy-2(phenylethynyl)phenyl]-2-propanone. Carson describes the synthesis of this intermediate from 1-(2-iodo-5-methoxyphenyl)-2-propanone in Example 38, which in turn is produced from 1-(3-methoxyphenyl)-2-propanone in Example 5. Such a synthesis involves difficulties in preparation of the prerequisite 1-(3-methoxyphenyl)-2-propanone and in the orientation of the iodine atom and in the iodination reaction. It can be seen that creation of a 1,2,4-substitution pattern on a phenyl ring can present synthetic problems and low yields. An object of this invention is thus a facile synthesis of the 1-(5-substituted-2-ethynylphenyl)-2-propanone intermediates of the Carson patent with good yields and control of the substitution on the positions of the phenyl ring.

SUMMARY OF THE INVENTION

Utilizing benzoquinone as a starting material, the invention takes advantage of its 1,4-substitution pattern as the basis for the synthesis of 1-(5-substituted-2-ethynylphenyl)-2-propanones. The synthesis is a 2-step addition sequence where an alkoxide of the formula (II) is condensed with a diketene (III) to produce a lactone of the formula (IV).

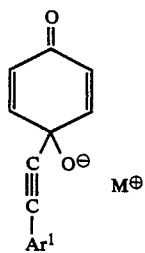

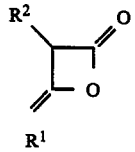

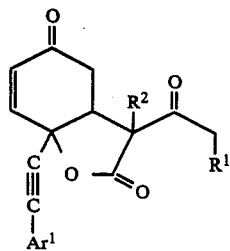

The lactone (IV) is then decarboxylated to yield the acetylenes of formula (I) which are intermediates for calcium blocking agents of U.S. Pat. No. 4,661,635.

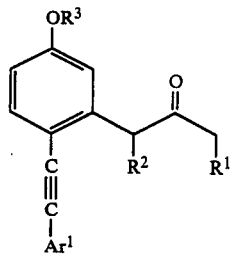

By proceeding through the lactone (IV), it has been found that excellent yields are obtained.

DETAILED DESCRIPTION OF THE INVENTION

The present invention comprises a process for the preparation of a 2-propanone of the following formula (I):

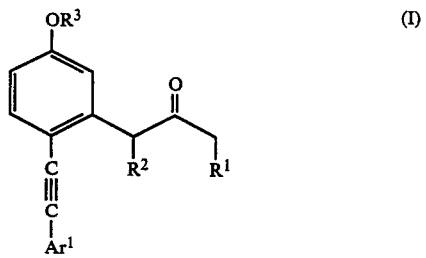

wherein
$R^1$ and $R^2$ are the same and are hydrogen or alkyl;
$R^3$ is hydrogen, alkyl or $COR^4$;
$R^4$ is alkyl, substituted alkyl, aryl or substituted aryl; and
$Ar^1$ is a phenyl ring or a 5- or 6-membered heterocyclic aromatic ring which rings may be independently substituted by one or more of alkyl, alkoxy, alkylthio, dialkylamino, carboxamido, halogen, fluoroalkyl or cyano, which comprises the steps of:
(a) condensing a carbinolalkoxide of the following formula (II) with a diketene derivative of the following formula (III):

wherein
$M^+$ is a metallic cation, to produce a lactone of the following formula (IV):

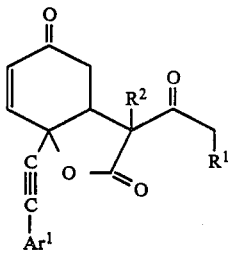

(IV)

and (b) decarboxylating the lactone of formula (IV) in the presence of water if $R^3$ is H, an alcohol of the formula $R^3OH$ if $R^3$ is alkyl or an anhydride of the formula $(R^4CO)_2O$ if $R^3$ is $COR^4$) to produce the 2-propanone of formula (I):

$R^1$ and $R^2$ are, in more detail, the same and are hydrogen; or alkyl of about 1 to 5 carbons with examples being methyl, ethyl or n-butyl. $R^3$ is hydrogen; alkyl of about 1 to 6 carbons such as methyl or ethyl; or $COR^4$ where $R^4$ is alkyl of about 1 to 6 carbons such as methyl, ethyl or iso-propyl; alkyl substituted by halo such as fluoro, chloro or bromo, e.g. $CF_3$; or substituted by alkoxy of about 1 to 6 carbons such as methoxy, ethoxy or n-butoxy, e.g. methoxymethyl; aryl such as phenyl; or aryl substituted by halo such as fluoro, chloro or bromo, by alkoxy of about 1 to 6 carbons such as methoxy, ethoxy or iso-propoxy, e.g. by nitro or by alkyl of about 1 to 6 carbons, e.g., 3-chlorophenyl, 4-methoxyphenyl, 2-nitrophenyl or 4-methylphenyl. Preferably, such substituted alkyl or aryl groups have 1, 2 or 3 such substituents.

$Ar^1$ is phenyl or a 5- or 6-membered heterocyclic aromatic ring containing 1, 2 or 3 heteroatoms such as nitroqen, sulphur or oxyqen with specific examples being thiophene, pyrrole, furan, pyrazole, imidazole, triazole, oxazole, thiazole, thiadiazole, pyridine, pyridazine, pyrimidine, pyrazine or triazine. Such heterocycles may be attached via a ring carbon atom to the acetylene moiety. The optional substitution on the $Ar^1$ ring is one or more, same or different, of alkyl, alkoxy or alkylthio of about 1 to 6 carbons, such as methyl, ethyl, methoxy, iso-propoxy or methylthio; dialkylamino of about 2 to 12 carbons, e.g., of about 1 to 6 carbons in each alkyl group, such as dimethylamino or N-ethyl-N-n-propylamino; halogen such as fluoro, chloro, or bromo; fluoroalkyl of about 1 to 6 carbons and one or more fluoro atoms with examples being 2,2,2-trifluoroethyl and trifluoromethyl. Such optional substituents may be attached at any available site on the phenyl or heterocyclic ring, in particular at the meta and para positions of a phenyl ring relative to the acetylene.

$M^+$ is a metallic cation, preferably having a valence of +1 or +2 with examples being the alkali and alkaline earth metals, in particular $Li^+$, $K^+$, $Mg^{++}$ and $Na^+$. Most preferably, $Li^+$ is used as $M^+$.

The term "independently" is used, e.g. with respect to $Ar^1$ substitution to indicate that when more than one of such substitution is possible, such substituents may be different from each other, e.g. $Ar^1$ may be 2-methyl-4-chlorophenyl.

Compounds of formula (I) prepared according to the process of the invention may exist in various isomeric forms, e.g., in view of the presence of an asymmetric carbon. It is understood that the invention process includes all such individual isomers and their racemates.

Also within the scope of the invention are processes of the invention in which the products are in the form of hydrates and other solvate forms.

Compounds of formula (I) are intermediates used in the synthesis of calcium blockers of the following formula (A):

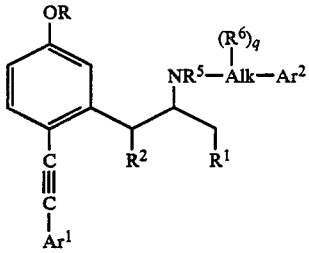

(A)

wherein

R is hydrogen or alkyl;

$R^1$, $R^2$ and $Ar^1$ are as defined for formula (I);

$R^5$ is hydrogen, alkyl, hydroxyalkyl, cycloalkyl or cycloalkylakyl or $R^5$ is independently selected from the group of the defined values of Alk-$Ar^2$;

$R^6$ is independently hydroxy, alkyl or phenyl;

Alk is straight chain alkylene of about 1 to 4 carbons;

q is 0, 1 or 2 or q is 3 if Alk is alkylene of about 2 to 4 carbons; and $Ar^2$ is a phenyl, phenoxy, thiophenoxy, naphthyl or a 5- or 6-membered heterocyclic aromatic ring which rings may be substituted independently by one or more alkyl, alkoxy, alkylthio, hydroxy, halogen, fluoroalkyl, nitro, amino or dialkylamino or by methylenedioxy at adjacent ring carbons;

To prepare final products of formula (A), the 2-propanone (I) where $R^3$ is hydrogen or alkyl may be used to reductively alkylate an amine of the formula $R^5NH$—$Alk(R^6)q$—$Ar^2$. The reductive alkylation may be carried out in one step from (I) and the amine using sodium cyanoborohydride as the reducing agent in a lower alkanol or acetonitrile as the solvent at neutral to mildly acidic pH at tèmperatures from 0° to 40° C., all as described in U.S. Pat. No. 4,661,635.

For 2-propanones of formula (I) where $R^3$ is $COR^4$, one must refunctionalize the $R^4CO$- moiety to hydroxy or alkoxy either before or after the reductive alkylation. To refunctionalize to hydroxy, the 2-propanone of formula (I) where R is $COR^4$ is saponified with a base such as NaOH or KOH in a protic or aprotic solvent such as EtOH, MeOH, DMF or DMSO to produce formula (I) where $R^3$ is hydrogen. From this hydroxy compound, one may alkylate with an alkyl halide such as methyl iodide or another alkylating agent such as dialkyl sulfate to produce the alkoxy 2-propanone of formula (I) where $R^3$ is alkyl.

For use in step (a), the carbinol alkoxide starting material is prepared by reacting an acetylide of the formula (V) with benzoquinone (VI):

(V)

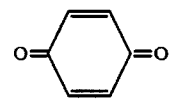

(VI)

where M+ and Ar¹ as defined above for formula (II). The reaction is conducted at a temperature of about −100° C. to +25° C. in the presence of an inert solvent. Particular temperatures are about −40° C. to 0° C. and solvents are non-halogenated inert aprotic solvents such as ethers, e.g. THF, DME and Et₂O. Reaction times will vary depending on the temperature and nature of the Ar¹ moiety. Preferably, a molar ratio for (V):(VI) of 1:1 is used in the reaction of (V) and (VI). The reaction conditions should be monitored to avoid the formation of diadducts to the benzoquinone, i.e., two 1,2-additions.

The acetylide (V) may be formed as known in the art with M moieties being alkali metals, e.g. Li, Na or K or magnesium directly attached to the acetylenic carbon, e.g. MgBr, MgCl or MgI. To prepare (V), the compound H—C≡C—Ar¹ is reacted with an M source such as an alkyl alkali metal, e.g. n-butyllithium, an alkali amide, e.g. sodium or lithium amide, an alkyl Grignard, e.g. methyl magnesium bromide or an alkali silylamide, e.g. potassium bis(trimethylsilyl)amide. Lithium is the preferred M species and various reagents for producing LiC≡C—Ar¹ are found in "The Chemistry of Organolithium Compounds" ed. by B. J. Wakefield, Pergamon Press, New York (1974).

The carbinol alkoxide (VI) of step (a) may be protonated to yield the dienone (IIa):

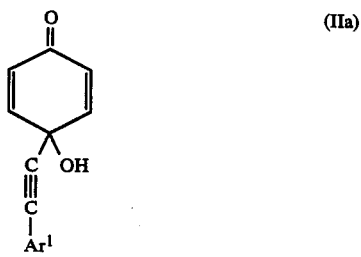

for storage or transport. The dienone may be subsequently deprotonated to reform the alkoxide (II). The protonation can be carried out with water and the deprotonation and reformation of the alkoxide can be accomplished with the M-containing reagent as described above.

Regarding the starting materials of formula (V), Ar¹-acetylenes as required may be prepared by the method of Ames et al. as described in Synthesis, 364 (1981). Treatment of Ar¹ iodides of the formula Ar¹-I with PdCl₂[(Ph)₃P]₂ or Pd(OAc)₂[(Ph)₃P]₂ and 2-methyl-3-butyn-2-ol affords acetylenic carbinols of the formula HOC(CH₃)₂—C≡C—Ar¹. Cleavage of the carbinol with an alkali metal hydroxide gives rise to the Ar¹-acetylenes.

In carrying out step (a), the carbinol alkoxide (II) is reacted with a diketene (III) to produce lactone (IV). The diketene derivatives covered in this application are either commercially available or may be prepared through methods known to the art. For examples see A. Sturzenegger et al., J. Org. Chem., 28, 920 (1963), C. M. Hill et al., J. Am. Chem. Soc., 75, 1084 (1953) and U.S. Pat. No. 4,614,546. The step (a) reaction may be carried out in the reaction mixture used for preparation of the carbinol alkoxide, although the acetylide (V) can be isolated and stored for use later. The reaction is carried out at about −100° C. to +100° C. although there is no advantage in reacting above 40° C. A preferred temperature range is −40° to +5° C. Suitable solvents are unreactive aprotic weakly polar solvents such as ethers, e.g. Et₂O, DME or THF. It is advantageous to use a co-solvent, e.g. DMF, although other dipolar aprotic solvents can be used, e.g. TMEDA, DMSO, DMPU, Tetramethylurea and HMPA. Yields are increased by using a co-solvent, e.g. as about 1 to 50% of the solvent volume.

In step (b), the lactone (IV) is decarboxylated to yield the 2-propanone (I). The reaction conditions are mild or strong base such as potassium carbonate or sodium hydroxide or mild acid such as acetic acid with sodium acetate or mild acid in R³OH. If mild base is used even in the presence of R³OH alcohol where R³ is alkyl, the Product (I) will have R³=H. Using a mild acid in an R³OH alcohol, the product (I) will have R³ being alkyl. If conducted in the presence of anhydride of the formula (R⁴CO)₂O where R⁴ is as described for formula (I), the decarboxylation and concurrent aromatization step (b) will result in formula (I) where R³ is COR⁴. The decarboxylation may be conducted at a temperature of about 100° to 200° C., particularly 130° to 150° C. in a high boiling solvent such as toluene or xylene or in an excess of the anhydride. Alkylation, e.g. methylation, of the 2-propanone of formula (I) where R³=H may be accomplished under conditions which are common in the art. For examples of similar methylations see: W. L. Mendelson et al., J. Org. Chem., 48, 4127 (1983) and R. A. Murphy, Jr. et al., Tetrahedron Lett., 25, 803 (1984).

In the following Examples, the following abbreviations are used: E (trans); Z (cis); bp (boiling point); mp (melting point); g (grams); mL (milliliters); glc (gas liquid chromatograph); hplc (high pressure liquid chromatography); NMR (nuclear magnetic resonance); N (normal); M (molar); THF (tetrahydrofuran); MeOH (methanol); DMF (N,N-dimethylformamide); DMPU (1,3-dimethyl-3,4,5,6-tetrahydro-2(1H)pyrimidone); LDA (lithium diisopropylamide); Ac(acetyl,CH₃CO—); RT (room temperature); DME (1,2-dimethoxyethane); DMSO (dimethylsulfoxide); EtOH (ethanol); HMPA (hexamethylphosphoramide); TMEDA (tetramethylethylenediamine); mmoles (millimoles); mg (milligrams); mm (millimeters); hr (hours); min (minutes); and C, H, N, etc. (the chemical symbols for the elements). Unless otherwise indicated, all temperatures are reported in degrees centigrade (°C.), all pressures in mm of mercury and all references to ether are to diethyl ether.

EXAMPLE 1

A. 3-Acetyl-3a,7a-dihydro-7a-(phenylethynyl) benzofuran-2,5(3H,4H)-dione (Formula (IV): R¹, R³=H and Ar¹=phenyl Under a sub-surface purge of nitrogen gas, a stirred mixture of phenylacetylene (817 g, 8.0 mol) and lithium amide (202.0 g, 8.8 mol) in 6.0 liters of dry THF was heated to reflux. At the reflux temperature, a vigorous reaction was initiated with evolution of a considerable volume of ammonia gas. The rate of ammonia evolution slowed substantially after 15 min. The reaction mixture was cooled slightly and decanted away from undissolved salts after standing briefly. The solution was added over 1-2 hr to a cold (−30° C.) suspension of 865.0 g (8.0 mol) of 1,4-benzoquinone in 6.0 liters of dry THF. The thick, blue slurry was stirred for 90 min at RT after the addition was completed whereupon 1.0 liter of DMF was added. Most of the solid was in solution and the reaction temperature was cooled to about −30° C. to −40° C. To the cold solution was added over 10 min 673.0 g (8.0 mol) of diketene and stirring was continued at this temperature for 0.5 hr. The temperature during the addition should not exceed −10° C. External cooling was removed and the reaction mixture warmed gradually over 1 hr to 5° C. The reaction mixture was then poured into a dilute solution of hydrochloric acid (2.0 liters of conc HCl in 20 liters of water). The crude product was extracted with dichloromethane (5.0 liters, then 3.0 liters). The combined lower phases were washed with 10 liters of water and the solvent was removed by vacuum distillation. The dark oily residue was triturated with 3.0 liters of Et$_2$O. The resultant solid was 1232 g (53.5% of theory) of product as a tan solid.

B. 1-[5-Hydroxy-2-(phenylethynyl)phenyl]-2-propanone

A mixture of 1232.0 g (4.2 mol) of the crude lactone product of Example 1A and 60.0 g of sodium acetate in 2.5 liters of glacial acetic acid was stirred and heated to reflux. Heating at reflux was continued for 2.0 hr. during which time carbon dioxide was evolved. The solution was diluted by addition of 1.5 liters of water and then stirred at ambient temperature for 2 to 3 hr. at which point solids began to precipitate. The mixture stood overnight without stirring. The solid product was collected by filtration and washed thoroughly with water. After drying in the air, there was obtained 560.0 g of phenolic product (53.0% of theory).

C. 1-[5-Methoxy-2-(phenylethynyl)phenyl]-2-propanone (Formula (I): $R^1$, $R^2$=H, $R^3$=CH$_3$, Ar$^1$=phenyl)

A solution of 559.0 g (2.2 mole) of the phenolic product of Example 1B in 3.6 liters of 95% ethanol was treated with a solution of 175.0 g (2.6 mol) of 85% potassium hydroxide in 0.57 liter of water and then 343.0 g (2.6 mol) of dimethyl sulfate was added. The solution was heated to reflux and refluxed for 2 hr. The solution was then cooled in an ice bath and the solid precipitate was collected by filtration. After washing with 50% ethanol, the product was dried in the air to give 532.0 g (91.0% of theory) of crude title ketone.

D. N-[2-(3,5-Dimethoxyphenyl)ethyl]-5-methoxy-α-methyl-2-(phenylethynyl)benzene ethanamine oxalate (Formula (A): R=CH$_3$, Ar$^1$=phenyl, $R^1$, $R^2$, $R^5$=H, Alk=CH$_2$CH$_2$, q=0, Ar$^2$=3,5-diOCH$_3$phenyl)

A solution of 1-[5-methoxy-2-(phenylethynyl)-phenyl]-2-propanone (1,000.00 g, 3.7 mol), 2-(3-,5-dimethoxyphenyl)ethylamine (670.5 g, 3.7 mol) and acetic acid (300.0 mL) in MeOH (3.0 liters) was added dropwise over 2-hr. to a stirred solution of sodium cyanoborohydride (232.5 g, 3.7 mol) in 1.5 liters of MeOH (under a purge of argon gas) at ambient temperature (20°-25° C.). The reaction temperature increased to 40°-50° C. by the end of the addition and stirring was continued for 12-16 hr as the reaction mixture cooled gradually back to ambient temperature. The reaction mixture was then diluted with 4.0 liters of 3.0% sodium hydroxide solution and 3.0 liters of water. The resulting mixture was twice extracted with dichloromethane (2.0 liters each). The solvents were removed by vacuum distillation to afford 1,605.0 g (101.0% of theory) of the crude product as a brownish oil which was converted to an oxalate salt by dissolution of the oil in 5.0 liters of MeOH, followed by addition of a solution of 333.1 g (3.7 mol) of oxalic acid in 1.0 liter of MeOH. The oxalate was precipitated by addition of 5.0 liters of Et$_2$O. The crystalline oxalate was collected by filtration to afford 1,423 g (74.0% of theory) of a light tan-colored solid (mp 123°-125° C.) after drying in the air for 48 hr.

Analysis indicated that the title product had a purity of 93.4% (area % by HPLC). This product is described in Example 59 of U.S. Pat. No. 4,661,635 as its butenedioate salt.

EXAMPLE 2

A. 4-Hydroxy-4-(phenylethnyl)-2.5-cyclohexadien-1-one (Formula IIA: Ar$^1$=phenyl)

A mixture of phenylacetylene (51.14 g, 0.5 mole) and dry THF (350 mL) was treated with lithium amide (11.24 g, 0.49 mole). The mixture was heated at reflux until ammonia evolution ceased. The reaction was cooled to RT then added rapidly to a slurry of benzoquinone (47.5 g, 0.439 mole) in THF (395 mL) at −10° C. to 0° C. The reaction was stirred for about 0.5 hr. then poured into an ice cold solution of ammonium chloride (68 g) in water (200 mL). The phases were separated and the aqueous phase was extracted with Et$_2$O. The combined organic phases were washed with saturated sodium chloride, dried over anhydrous sodium sulfate, filtered and concentrated in vacuo. The residue was slurried with 1:1 EtOAc:petroleum ether, filtered and air dried to give 69.8 g (75.6%) of a light tan solid, the title compound.

Particularly in scaling up this reaction, it is advantageous to prepare the lithium phenylacetylide by suspending the lithium amide in THF, heating to reflux and carefully adding the phenylacetylene to the mixture whereby the reaction is controlled.

3-Acetyl-3a, 7a-dihydro-7a-(phenylethynyl)benzofuran-2,5(3H,4H)dione (Formula (IV): $R^1$, $R^2$=H and Ar$^1$=phenyl)

4-Hydroxy-4-(phenylethynyl)-2,5-cyclohexadien-1-one, the product of Example 2A, (10.5 g, 0.05 mole) was dissolved in dry THF (100 mL). The reaction was cooled to −30° C. and treated with 1.96M LDA in cyclohexane (25.5 mL, 0.05 mole). During the addition of the LDA solution, a beige-colored slurry formed. The reaction was cooled to −78° C. and stirred at that temperature for 40 min. Dry DMF (10 mL) was added. The reaction immediately became homogeneous. Diketene (6.3 mL, 0.08 mole) was added rapidly and the reaction was stirred for 20 min before an additional portion of diketene (4.0 mL 0.05 mole) was added. The stirred reaction was allowed to warm slowly to 0° C., then quenched into ice (300 g) and concentrated hydrochloric acid (45 mL). The resulting mixture was extracted with CH$_2$Cl$_2$. The combined extracts were washed with water, dried over anhydrous sodium sulfate overnight, filtered and concentrated. The resulting solution was concentrated in vacuo. The residue was treated with Et$_2$O (300 mL) and cooled to 0° C. for 1 hr. The resulting solid was isolated by filtration and washed with Et$_2$O to yield 7.8 g (53%) of the title compound as a light tan solid.

EXAMPLE 3

A. 1-[5-Hydroxy-2-(phenylethynyl)phenyl]-2-propanone (Formula (I): $R^1$, $R^2$, $R^3$=H, Ar$^1$=phenyl)

3-Acetyl-3a,7a-dihydro-7a-(phenylethynyl)benzofuran-2,5-(3H,4H)-dione, the product of Example 1A, (1.5 g, 5 mmole) was dissolved in MeOH (50 mL) and water (10 mL). Anhydrous potassium carbonate 7.1 g, 50 mmole) was added and the mixture was heated at reflux for 45 min. The reaction was quenched into ice cold 3N hydrochloric acid and extracted with EtOAc (3×50 mL). The combined extracts were washed with water (50 mL) and brine (2×50 mL), dried over anhydrous sodium sulfate, filtered and concentrated. The residue was purified by flash column chromatography (silica gel; 3:1::hexane:EtOAc) to give 0.84 g (65%) of the title compound as a light brown crystalline solid.

EXAMPLE 4

A. 1-[5-Acetoxy-2-(phenylethynyl)phenyl]-2-propanone (Formula (I): $R^1$, $R^2$=H, $R^3$=Ac, $Ar^1$=phenyl)

3-Acetyl-3a,7a-dihydro-7a-(phenylethynyl)benzofuran-2,5(3H,4H)dione, the product of Example 1A, (10.0 g, 34 mmole) and acetic anhydride (25 mL) were placed in a 100 mL flask and heated at reflux overnight under argon. Heating was stopped and the reaction was treated with water (25 mL) and stirred for 1 hr. The reaction was poured into water and extracted with $Et_2O$. The combined ether extracts were washed with water and saturated sodium bicarbonate, dried over anhydrous sodium sulfate, filtered and concentrated to yield 9.4 g of crude product. Chromatography of the crude product over silica gel, using methylene chloride as eluent, gave 4.2 g of pure 1-[5-Acetoxy-2-(phenylethynyl)phenyl]-2-propanone product as a viscous oil.

B. 1-[5-Hydroxy-2-(phenylethynyl)phenyl]-2-propanone (Formula (I): $R^1$, $R^2$, $R^3$=H, $Ar^1$=phenyl)

1-[5-Acetoxy-2-(phenylethynyl)phenyl]-2-propanone (3.3 g, 11 mmole) was dissolved in MeOH (15 mL) and treated with 50% sodium hydroxide solution (1.8 g, 22 mmole) under argon. The reaction was stirred for 1 hr then poured into dilute hydrochloric acid and extracted with diethyl ether. The combined organic extracts were washed with water and brine, dried over anhydrous sodium sulfate, filtered and concentrated. The product was dried under vacuum to yield 2.78 g (98%) of the title compound.

EXAMPLE 5

A. 3-Acetyl-3a,7a-dihydro-7a-(phenylethynyl)benzofuran-2,5(3H,4H)-dione (Formula (IV): $R^1$, $R^3$=H and $Ar^1$=phenyl)

Phenylacetylene (1 mL, 9.3 mmole) was placed in dry THF (10 mL) in a dry, 50 mL, 3-necked, round bottomed flask fitted with a mechanical stirrer, thermometer and argon inlet. The solution was cooled to −78° C. and treated with 1.6M n-butyllithium (5.8 mL, 9.3 mmole) in hexane. The reaction was stirred at −78° C. for 30 min, warmed to 0° C., then recooled to −78° C. Benzoquinone (1 g, 9.3 mmole) and dry THF (10 mL) were added, under argon, to a separate 100 mL, 3-necked, round bottomed flask. The mixture was cooled to −78° C. and treated with the lithium phenylacetylide solution prepared above. The flask which contained the lithium phenyacetylide solution was washed with dry THF (10 mL) and the solvent was added to the larger flask. Upon addition of the lithium phenylacetylide, the reaction mixture turned dark blue. The reaction was stirred for 20 min at −78° C. then dry DMPU (18 mL, 0.15 mole) was added. The reaction was stirred for five min before diketene (0.8 mL, 10.2 mmole) in THF (10 mL) was added. The reaction was stirred for 1 hr at −78° C., then allowed to warm to room temperature, stirred overnight and concentrated in vacuo. The residue was treated with water (50 mL) and saturated ammonium chloride (50 mL), acidified with 3N hydrochloric acid, and extracted with $CH_2Cl_2$ (4×75 mL). The combined $CH_2Cl_2$ extracts were washed with water (50 mL) and brine (2×50 mL), dried over anhydrous sodium sulfate, filtered and concentrated. The residue was dissolved in $Et_2O$ (150 mL), and the solution was washed with water (3×50 mL and 1×75 mL) and brine (75 mL), dried over anhydrous sodium sulfate, filtered and concentrated in vacuo. The residue was purified by flash column chromatography (silica gal; eluting with hexane: EtOAc (4:1) to yield 2.4 g (88%) of the title compound. Crystallization from acetone/ethyl acetate gave a white solid, m.p. 168°–171° C. (dec.).

B. 1-[5-Methoxy-2-(phenylethynyl)phenyl]-2-propanone (Formula (I): $R^1$, $R^2$=H, $R^3$=Ac, $Ar^1$=phenyl)

3-Acetyl-3a,7a-dihydro-7a-(phenylethynyl)benzofuran-2,5(3H,4H)dione, (1.75 g 6 mmole), pyridinium chloride (1.5 g, 13 mmole) and MeOH (50 mL) were placed in a 100 mL round bottomed flask and heated at reflux for 2 hr. The solvent was removed under reduced pressure and the residue was partitioned between $Et_2O$ and water. The ether phase was washed with 3N hydrochloric acid, dried over anhydrous sodium sulfate, filtered and concentrated. The residue was recrystallized from ethanol (10 mL) to give 0.8 g (50%) of the title compound as a light yellow solid, m.p. 63°–65° C.

EXAMPLES 6–11

3-Acetyl-3a, 7a-dihydro-7a-(phenylethynyl)benzofuran-2,5(3H,4H)-dione (Formula (IV): $R^1$, $R^2$=H, $R^3$=Ac, $Ar^1$=phenyl)

EXAMPLE 6

Phenylacetylene (32.1 g, 0.3 mole) was placed in dry THF (250 mL) containing lithium amide (7.0 g, 0.3 mole) in a dry, 500 mL, 3-necked, round bottomed flask fitted with a magnetic stirrer and nitrogen inlet. Nitrogen was blown through the mixture while it was heated at reflux until ammonia evolution ceased. The reaction was cooled to 0° C. Benzoquinone (30 g, 0.28 mole) and dry THF (250 mL) were added, under nitrogen, to a separate 1000 mL, 3-necked, round bottomed flask. The reaction was cooled to −10° C. and treated with the lithium phenylacetylide solution prepared above at such a rate that the temperature was maintained at less than 0° C. Upon addition of the lithium phenylacetylide, the reaction mixture turned dark blue. The reaction was stirred for 45 min at 0° C., then cooled to −10° C. and dry TMEDA (100 mL) was added. The reaction was stirred while diketene (24 mL) was added to produce an exotherm. The reaction was allowed to warm to room temperature and stirred overnight. The reaction mixture was quenched with dilute sulfuric acid, the organic phase was separated and concentrated under reduced pressure. The residue was triturated with EtOAc and the resulting solid was isolated by filtration to yield 23.8 g (29% of the title compound as a tan solid.

EXAMPLE 7

The procedure of Example 6 was followed to produce the dark blue reaction mixture. Instead of being stirred for 45 min, the reaction was stirred for 30 min. at 0° C., then DMPU (150 mL) was added in place of TMEDA. The reaction was cooled to −10° C. and stirred while diketene (24 mL) was added at a rate such that the temperature was maintained below 0° C. The reaction was allowed to warm to RT and stirred overnight. The reaction mixture was quenched with ice-cold dilute hydrochloric acid, and extracted with $CH_2Cl_2$. The combined organic phases were separated, dried over sodium sulfate, filtered and concentrated under reduced pressure. The residue was triturated with EtOAc and the resulting solid was isolated by filtration to yield 53.6 g (65%) of the title compound as a tan solid.

EXAMPLE 8

Following Example 6, a dark blue reaction mixture was produced. Instead of stirring for 45 min, the reaction was stirred for 30 min. at 0° C., cooled to −10° C., no TMEDA was added, and stirred while diketene (24 mL) was added slowly. The reaction temperature gradually rose to 10° C. then rapidly exothermed to 40° C. The reaction was allowed to cool to RT and stirred overnight. The reaction mixture was quenched with ice-cold dilute hydrochloric acid (100 mL) and water (900 mL) and extracted with $CH_2Cl_2$. The combined organic phases were separated, dried over sodium sulfate, filtered and concentrated under reduced pressure. The residue was triturated with EtOAc and the resulting solid was isolated by filtration to yield 23.6 g (29%) of the title compound as a tan solid. Chromatography (silica gel; 25% EtOAc in hexane) of the mother liquors resulted in isolation of an additional 11.3 g (14%) of the desired product.

EXAMPLE 9

Phenylacetylene (33.3 g, 0.32 mole) was placed in dry THF (250 mL) containing lithium amide (7.5 g, 0.32 mole) in a dry 500 mL, 3-necked, round bottomed flask fitted with a magnetic stirrer and nitrogen inlet. Nitrogen was blown through the mixture while it was heated at reflux until ammonia evolution ceased. The reaction was cooled to 0° C. Benzoquinone (34.5 g, 0.32 mole) and dry THF (150 mL) were added, under nitrogen, to a separate 1000 mL, 3-necked, round bottomed flask. The reaction was cooled to −20° C. and treated with lithium phenylacetylide solution prepared above at such a rate that the temperature was maintained at less than 0° C., the reaction mixture turning dark blue. The reaction was stirred for 30 min at −10° C. before 1,1,3,3-tetramethylurea (75 mL) was added. The reaction as cooled to −20° C. and stirred while diketene (30 mL) in dry THF (150 mL) was added slowly. The reaction temperature gradually rose to 10° C. After addition was complete, the reaction was stirred at 0° C. to 10° C. for 45 min, quenched into ice water (1500 mL) containing concentrated HCl (100 mL), stirred for 30 min and the product was isolated by filtration. The filter cake was air dried overnight, then suspended in 2-propanol (100 mL) and filtered. The filter cake was washed with $Et_2O$ (50 mL), air dried and dried under vacuum to give 63.7 g of a tan solid which assayed as 80.2% pure (54.5% yield).

EXAMPLE 10

Phenylacetylene (32.4 g, 0.31 mole) was placed in dry THF (250 mL) containing lithium amide (7.14 g, 0.3 mole) in a dry, 500 mL, 3-necked round bottomed flask fitted with a magnetic stirrer and nitrogen inlet. Nitrogen was blown through the mixture while it was heated at reflux for about 1 hr until ammonia evolution ceased. The reaction was cooled to 0° C. Benzoquinone (30 g, 0.2B mole) and dry THF (250 mL) were added, under nitrogen, to a separate 1000 mL, 3-necked round bottomed flask. The reaction was cooled to −10° C. and treated with lithium phenylacetylide solution prepared above at such a rate that the temperature was maintained at less than 0° C. Upon addition of the lithium phenylacetylide, the reaction mixture turned dark blue. The reaction was stirred for 15 min, cooled to −20° C. and treated with dry DMF (100 mL). The reaction was cooled to −70° C. and stirred while diketene (25 mL) was added over a period of less than 5 min. The reaction temperature rose to −60° C. After addition was complete, the reaction was allowed to warm to 10° C. over a period of 1.5 hr then quenched into ice water (900 mL) containing concentrated HCl (100 mL). The resulting mixture was stirred for several min, diluted with water (100 mL) and the product isolated by filtration. The filter cake was suspended in 2-propanol (75 mL), filtered and the filter cake was washed with 2-propanol (50 mL), air dried and dried under vacuum to give 58.4 g of a tan solid which assayed as 98% pure (69.6% yield).

EXAMPLE 11

Phenylacetylene (30.47 g, 0.3 mole) was placed in dry THF (250 mL) containing lithium amide (7.1 g, 0.3 mole) in a dry, 500 mL, 3-necked, round bottomed flask fitted with a magnetic stirrer and nitrogen inlet. Nitrogen was blown through the mixture while it was heated at reflux for about 1 hr until ammonia evolution ceased. The reaction was cooled to 0° C. Benzoquinone (30 g, 0.2B mole) and dry THF (200 mL) were added, under nitrogen, to a separate 1000 mL, 3-necked, round bottomed flask. The reaction was cooled to −30° C. and treated with the lithium phenylacetylide solution prepared above at such a rate that the temperature was maintained at less than −5° C. Upon addition of the lithium phenylacetylide, the reaction mixture turned dark blue. The reaction was stirred for 30 min at −10° C. and treated with dry DMF (100 mL). The reaction was maintained at −10° C. and added via cannula to a solution of diketene (30 mL) in THF (150 mL) at −20° C. After addition was complete (45 min), the reaction was stirred at −10° C. to 0° C. for 45 min. The reaction mixture was quenched into ice water (1500 mL) containing concentrated HCl (100 mL), stirred for 2 hr and the product was isolated by filtration. The filter cake was suspended in 2-propanol (50 mL), filtered and the filter cake was washed with 2-propanol (25 mL), air dried and dried under vacuum to give 62.8 g of a tan solid which assayed as 88.8% pure (67.7% yield), m.p. 157°–160° C. (dec.).

What is claimed is:

1. A process for the preparation of a 2-propanone of the following formula (I):

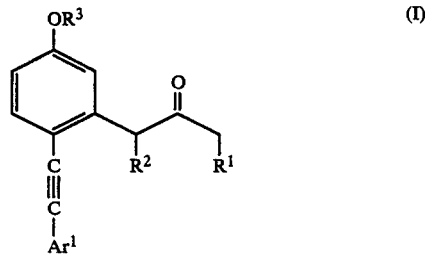

wherein $R^1$ and $R^2$ are the same and are hydrogen or alkyl;

$R^3$ is hydrogen, alkyl or $COR^4$;

$R^4$ is alkyl, substituted alkyl, aryl or substituted aryl; and $Ar^1$ is phenyl or a 5- or 6-membered heterocyclic aromatic ring which rings may be independently substituted by one or more of alkyl, alkoxy, alkylthio, dialkylamino, carboxamido, halogen, fluoroalkyl or cyano, which comprises the steps of:

(a) condensing a carbinol of the following formula (II) with a diketene derivative of the following formula (III):

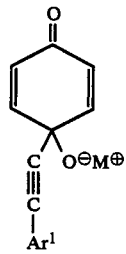
(II)

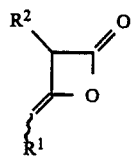
(III)

wherein
M is a metallic cation, to produce a lactone of the following formula (IV):

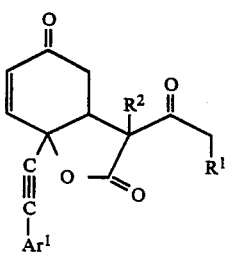
(IV)

and (b) decarboxylating the lactone of formula (IV) in the presence of an $R^3$ source to produce the 2-propanone of formula (I).

2. The process of claim 1, wherein $R^1$ and $R^2$ are hydrogen or alkyl of about 1 to 5 carbons; $R^3$ is hydrogen, alkyl of about 1 to 6 carbons or $COR^4$; $R^4$ is alkyl of about 1 to 6 carbons, alkyl of about 1 to 6 carbons substituted by one or more of halo and alkoxy of about 1 to 6 carbons, phenyl or phenyl substituted by one or more of halo, alkoxy of about 1 to 6 carbons, nitro or alkyl of 1 to 6 carbons.

3. The process of claim 1, wherein $Ar^1$ is phenyl or a 5- or 6-membered heterocyclic ring containing 1, 2 or 3 nitrogen, sulphur or oxygen heteroatoms and said substitution on said ring is alkyl, alkoxy or alkylthio of about 1 to 6 carbons, dialkylamino of about 2 to 12 carbons, carboxamido, fluoro, chloro, bromo, fluoroalkyl of about 1 to 6 carbons or cyano.

4. The process of claim 1, wherein $Ar^1$ is phenyl.

5. The process of claim 1, wherein $M^+$ is $Li^+$, $Na^+$, $Mg^{++}$ or $K^+$.

6. The process of claim 5, wherein $M^+$ is $Li^+$.

7. The process of claim 1, wherein said condensation step (a) is conducted at a temperature of about $-100°$ to $+100°$ C.

8. The process of claim 7, wherein said temperature is about $-40°$ to $+5°$ C.

9. The process of claim 1, wherein said condensation step (a) is conducted in the presence of at least two solvents.

10. The process of claim 9, wherein one of said solvents is an aprotic weakly polar solvent and a second solvent is a dipolar aprotic solvent.

11. The process of claim 10, wherein said aprotic weakly polar solvent is an ether.

12. The process of claim 1, wherein said decarboxylation step (b) is conducted at a temperature of about 55° to 150° C.

13. The process of claim 1, wherein said decarboxylation step (b) is conducted in the presence of $R^3OH$ or $(R^4CO)_2O$.

* * * * *